US009057729B2

(12) United States Patent
Hendriks et al.

(10) Patent No.: US 9,057,729 B2
(45) Date of Patent: *Jun. 16, 2015

(54) VITRO METHOD OF DETECTING AND/OR DIAGNOSING CANCER USING UV LIGHT BASED DNA IMAGE CYTOMETRY

(75) Inventors: Bernardus Hendrikus Wilhelmus Hendriks, Eindhoven (NL); Erik Robbert Vossenaar, De Meern (NL); Gerhard Spekowius, Roetgen (DE); Nijs Cornelis Van Der Vaart, Rosmalen (NL); Stein Kuiper, Vught (NL)

(73) Assignee: Koninklijke Philips N.V., Eindhoven (NL)

( * ) Notice: Subject to any disclaimer, the term of this patent is extended or adjusted under 35 U.S.C. 154(b) by 1102 days.

This patent is subject to a terminal disclaimer.

(21) Appl. No.: 12/305,399
(22) PCT Filed: May 14, 2007
(86) PCT No.: PCT/IB2007/051810
§ 371 (c)(1),
(2), (4) Date: Dec. 18, 2008
(87) PCT Pub. No.: WO2008/001235
PCT Pub. Date: Jan. 3, 2008

(65) Prior Publication Data
US 2009/0197272 A1 Aug. 6, 2009

(30) Foreign Application Priority Data
Jun. 29, 2006 (EP) .................................... 06116336
Aug. 4, 2006 (EP) .................................... 06118438

(51) Int. Cl.
*C12Q 1/68* (2006.01)
*G01N 1/30* (2006.01)
(Continued)

(52) U.S. Cl.
CPC ................ *G01N 33/582* (2013.01); *C12Q 1/68* (2013.01); *G01N 15/147* (2013.01); *G01N 21/33* (2013.01);
(Continued)

(58) Field of Classification Search
CPC ...... C12Q 1/68; G01N 21/33; G01N 21/6458; G06T 2207/10056
USPC .............. 435/6.1, 40.5, 448; 436/64; 250/373
See application file for complete search history.

(56) References Cited

U.S. PATENT DOCUMENTS 3,327,119 A * 6/1967 Kamentsky ................. 250/461.2
3,675,768 A * 7/1972 Legorreta-Sanchez ........... 209/4
(Continued)

FOREIGN PATENT DOCUMENTS

SU 1451598 A1 1/1989

OTHER PUBLICATIONS

Toikkanen et al, The prognostic significance of nuclear DNA content in invasive breast cancer—a study with long-term follow up, 1989, Br. J. Cancer, 60, 693-700.*
Belien et al, Confocal DNA Cytometry: A Contour-Based Segmentation Algorithm for Automated Three-Dimensional Image Segmentation, 2002, Cytometry, 49, 12-21.*
Ploeger et al, Implementation of accurate and fast DNA cytometry by confocal microscopy in 3D, 2005, Cellular Oncology, 27, 225-230.*
Ecker et al, Cytomics: An Entry to Biomedical Cell Systems Biology, Cytomics Goes 3D: Toward Tissomics, 2005, Cytometry Part A 65A:1-3.*

(Continued)

Primary Examiner — Narayan Bhat

(57) ABSTRACT

The invention relates to a method of determining in vitro the amount of nuclear DNA within a human or animal cell using UV absorption measurement with UV light. The invention also relates to a method for detecting in vitro cancerous cells in a biological sample relying on the aforementioned principles. The invention also relates to an in vitro method of diagnosing or predicting the likely occurrence of cancer in a human or animal subject.

6 Claims, 3 Drawing Sheets

(51) Int. Cl.

| | |
|---|---|
| C12N 15/01 | (2006.01) |
| G01N 33/48 | (2006.01) |
| G01J 1/42 | (2006.01) |
| G01N 33/58 | (2006.01) |
| G01N 15/14 | (2006.01) |
| G01N 21/33 | (2006.01) |
| G01N 33/50 | (2006.01) |
| G01N 33/53 | (2006.01) |
| G01N 33/574 | (2006.01) |
| G06T 7/00 | (2006.01) |
| G06T 7/40 | (2006.01) |

(52) U.S. Cl.
CPC ........ *G01N 33/5035* (2013.01); *G01N 33/5076* (2013.01); *G01N 33/5308* (2013.01); *G01N 33/574* (2013.01); *G06T 7/0012* (2013.01); *G06T 7/401* (2013.01); *G06T 2207/10056* (2013.01); *G06T 2207/30024* (2013.01)

(56) References Cited

U.S. PATENT DOCUMENTS

| | | | | |
|---|---|---|---|---|
| 3,699,336 | A * | 10/1972 | Ehrlich et al. | 250/461.2 |
| 4,767,717 | A * | 8/1988 | Baisden | 436/64 |
| 5,932,872 | A | 8/1999 | Price | |
| 6,165,734 | A | 12/2000 | Garini | |
| 6,696,241 | B2 * | 2/2004 | Thompson et al. | 435/4 |
| 2004/0001618 | A1 * | 1/2004 | Johnson et al. | 382/131 |
| 2004/0197839 | A1 | 10/2004 | Daniely | |
| 2005/0272073 | A1 | 12/2005 | Vaisberg | |
| 2007/0097369 | A1 * | 5/2007 | Shimada | 356/417 |

OTHER PUBLICATIONS

Reeder, Jay E. et al "DNA Cytometry and Chromosome 9 Aberrations by Fluorescence in SITU Hybridization of Irrigation Specimens from Bladder Cancer Patients" 1998 Elsevier Science Inc. vol. 51, No. 5 pp. 58-61.

Short, Michael A. et al "Changes in Nuclei and Peritumoral Collagen within Nodular Basal Cell Carcinomas via Confocal Micro-Raman Spectroscopy" Journal of Biomedical Optics, vol. 11, No. 3, May 2006, p. 34004.

Abramowitz, Mortimer et al "Fluorescence Microscopy: Combination Methods with Phase Contrast" Aug. 1, 2003, p. 1-3.

Kozubek, M. et al "High-Resolution Cytometry of FISH Dots in Interphase Cell Nuclei" Cytometry vol. 36, No. 4, Aug. 1, 1999, pp. 279-293.

Kavantzas, N. et al "Nuclear/Nucleolar Morphometry and DNA Image Cytometry as a Combined Diagnostic Tool in Pathology of Prostatic Carcinoma" Journal of Experimental and Clinical Cancer Research, vol. 20, No. 4, Dec. 2001, pp. 537-542.

Notingher, I. et al "Raman Microspectroscopy: A Noninvasive Tool for Studies of Individual Living Cells in Vitro" Expert Review of Medical Devices, Mar. 2006, vol. 3, No. 2 pp. 215-234.

Swinson, B. et al "Optical Techniques in Diagnosis of Head and Neck Malignancy" Oral Oncology, Mar. 2006, vol. 42, No. 3, pp. 221-228.

Fernandez-Lopez, F. et al "Prognostic Value of Nuclear Morphometry in Colorectal Cancer" Diseases of the Colon and rectum, vol. 42, No. 3, Mar. 1999, pp. 386-392.

Biesterfeld, Stefan et al "DNA Image Cytometry in the Differential Diagnosis of Endometrial Hyperplasia and Adenocarcinoma" Analytical and Quantitative Cytology and Histology, vol. 23, No. 2, Apr. 2001, pp. 123-128.

* cited by examiner

VITRO METHOD OF DETECTING AND/OR DIAGNOSING CANCER USING UV LIGHT BASED DNA IMAGE CYTOMETRY

SUBJECT OF THE INVENTION

The invention relates to a method of determining in vitro the amount of nuclear nucleic acids within the nucleus of a human or animal cell by measuring UV absorbance of nuclear nucleic acids.

The invention also relates to a method of detecting in vitro cancerous cells in a biological sample that relies on UV absorbance of nuclear nucleic acids.

The invention further relates to an in vitro method of diagnosing and/or predicting cancer in a human or animal subject with the method being based on UV absorbance of nuclear nucleic acids.

BACKGROUND OF THE INVENTION

Early detection of cancer is a key feature in treating cancer patients. There are various possibilities of detecting cancerous cells in a biological sample and thus to diagnose an existing cancer or at least to estimate the likelihood of future cancer development. These different approaches comprise physical examination of cancer tissue, morphological characterization of cancerous cells, immunohistochemical staining and characterization of cellular structures such as membranes and the nucleus, measuring the expression of tumour specific factors, etc.

One possibility of detecting cancerous cells is so called DNA cytometry, which measures the amount of nuclear DNA in order to detect deviations from normal DNA content. It is assumed that if a cell as a consequence of mutagenic events comprises less or more DNA than a known standard, which is known to be of a non-cancerous, i.e. "healthy" or "normal" type, this deviation in DNA content can be indicative of major chromosomal rearrangements and thus ongoing cancer development.

Quantitation of nuclear DNA by nucleic acids specific stains is thus increasingly coming into practice in both research and clinical applications in the context of cancer diagnosis.

The measurement of nuclear DNA content by either flow or image cytometry is based inter alia on the assumptions that (i) the amount of stain bound to DNA is proportional to the amount of DNA present and that (ii) the optical signal generated from the stain by emission, absorption or transmission is proportional to the amount of stain.

One DNA specific staining procedure which is typically used for the purpose of measuring nuclear DNA by DNA image cytometry is an acid-based reaction named after Feulgen and Rossenbeck, often simply referred to as the Feulgen reaction. Actually the Feulgen reaction is a chromogenic reaction in which DNA is hydrolyzed by an acid to create a purine-free DNA (i.e. so-called apurinic acid, APA) with free aldehyde groups. These are then reacted with a Schiff's reagent containing a dye that binds covalently to the free aldehyde groups.

While the Feulgen reaction is specific for DNA, it suffers from various drawbacks. It is a time-consuming and rather elaborate reaction that needs to be carefully controlled and validated in order to yield reproducible and meaningful results. One problem arises from the fact that HCl, which is commonly used for the removal of the purine bases, hydrolyzes the APA into smaller fragments. However, fragmentation of the APA molecules leads to removal of these fragments from the cell nucleus and thus to loss of stainable DNA material.

Therefore, attempts have been made in the art to rely on a combination of morphological characterization, immunohistochemical stains and DNA stains for reliably detecting cancerous cells and diagnosing cancer.

US 2004/0197839 A1 discloses the concomitant use of two different type of stains for identifying cancerous cells in which one stain e.g. detects morphological characteristics whereas a second (immunological) stain e.g. measures the expression of a tumour-specific marker.

However, there is a continuing need for methods that allow a reliable, rapid and efficient way of measuring the amount of nuclear DNA and detection of cancerous cells and cancers.

OBJECT AND SUMMARY OF THE INVENTION

It is an object of the present invention to provide a method for determining the amount of nucleic acids in the nucleus of a cell. These nucleic acids may be double stranded such as DNA.

It is also an object of the present invention to provide a method of detecting the presence of cancerous cells in a biological sample to be tested.

It is a further object of the present invention to provide a method that allows diagnosing the presence of cancer and/or the likely development of cancer in a human or animal subject.

In order to achieve the above-defined objects, methods as defined in independent claims are provided. Some of the preferred embodiments of the invention can be found inter alia in the dependent claims.

According to one embodiment of the invention, a method of determining in vitro the amount of nuclear nucleic acids such as nuclear DNA in at least one cell being present in at least one biological sample is provided wherein said method comprises the steps of:

a) determining in vitro the position and/or dimensions of the nucleus within said cell, b) determining in vitro the UV absorbance within the nucleus' boundaries as determined in a).

In one exemplary embodiment, the position and/or dimensions of the nucleus may be (roughly) determined in said at least one cell by using UV light and/or phase-contrast microscopy. If UV light is used in step a), one will preferably use UV light of a wavelength between approximately 240 nm and approximately 280 nm. Particularly preferred are wavelengths such as approximately 250 nm, 255 nm or 260 nm.

In another exemplary embodiment, one uses UV light of a wavelength between approximately 240 nm and approximately 280 nm for measuring UV absorbance in step b). Particularly preferred are wavelengths such as approximately 250 nm, 255 nm or 260 nm.

In yet another embodiment one can contact said at least one cell with at least one fluorescent marker which is capable of interacting with double stranded nucleic acids within said at least one cell and then determines the nuclear signal intensity of said at least one fluorescent marker being bound to nuclear double stranded nucleic acids by UV absorbance in step b). To this end one can use e.g. UV light with a a wavelength between approximately 240 nm and approximately 280 nm.

However, in other exemplary embodiments of the present invention, it is not necessary to visualize the nuclear nucleic acids such as DNA of said cell by e.g. immunohistochemical stains, chemical reactions such as the Feulgen reaction or fluorescent markers.

Thus, the methods of the present invention comprises various embodiments which realize the basic concept of determining the position and/or dimensions of the nucleus within a cell and determining the UV absorbance within the nucleus' boundaries. For determining the nucleus position and/or dimensions which is equivalent to determining the nucleus' boundaries one can use phase contrast microscopy with visible light as well as detection approaches with UV light. For determining the UV absorbance of the nucleus one may rely solely on UV measurements without adding fluorescent markers that are capable of interacting with double stranded nucleic acids or one may use such markers.

Thus, one can in principle localize the cell nucleus with phase contrast microscopy and determine UV absorbance of the nucleus without using the above described markers, one can localize the cell nucleus with phase contrast microscopy and determine UV absorbance of the nucleus using the above described markers, one can use UV absorbance measurements for localizing the nucleus and measuring nuclear UV absorbance without the above described markers, and one can use UV absorbance measurements for localizing the nucleus and measuring nuclear UV absorbance with the above described markers, etc.

The invention in two of its exemplary embodiments is concerned with localizing the cell nucleus with phase contrast microscopy and determining UV absorbance of the nucleus using the above described markers, or with using UV absorbance measurements for localizing the nucleus and measuring nuclear UV absorbance without the above described markers. These two embodiments will be described in further detail hereinafter. However, the skilled person is clearly aware that, if certain aspects such as preferred wavelengths, the nature of the markers, the detection devices to be used etc., are discussed in the context of these two embodiments, these explanations equally apply two the other embodiments of the invention as mentioned above unless it is explicitly indicated otherwise. The definition of terms such as "cell", "cancerous cell", "sample", "aneuploidity" etc., of course, have the same meaning throughout the various embodiments of the invention unless indicated otherwise. The various methods as envisaged by the present invention can also be used for the same purposes.

In one exemplary embodiment of the present invention, the aforementioned methods for determining the amount of nuclear nucleic acids such as DNA within a cell may be used to detect in vitro at least one cancerous cell within at least one biological sample.

In a further embodiment of the aforementioned methods, the nuclear UV absorbance which can also be designated as nuclear signal intensity can be used to calculate the (aneu) ploidy state of the cell.

This can be done by referencing the obtained nuclear UV absorbance to a nuclear UV absorbance obtained under substantially comparable or identical conditions for a cell for which one knows that it is of a non-cancerous type and for which the nuclear DNA content is known.

In yet another embodiment of the present invention, an aneuploidy state deviating by at least 10% from 2 or 4 will be considered to be indicative of a cancerous cell.

In one embodiment of the present invention, methods of determining the amount of nuclear nucleic acids such as DNA within a cell as described above are used to detect at least one cancerous cell in at least one biological sample which is associated with a cancer selected from the group comprising leukemia, lymphoma, brain cancer, cerebrospinal cancer, bladder cancer, prostate cancer, breast cancer, cervical cancer, uterus cancer, ovarian cancer, kidney cancer, oral and throat cancer, esophageal cancer, lung cancer, colon rectal cancer, pancreatic cancer and melanoma.

In yet another embodiment of the present invention, methods of determining the amount of nuclear nucleic acids such DNA within a cell as described above are performed on at least one cell of a biological sample wherein the biological sample is selected from the group comprising bone marrow cells, lymph nodes cells, mucosal samples, peripheral blood samples, cerebrospinal fluid samples, urine samples, effusion samples, fine needle aspirates, peripheral blood scrapings, skin scrapings, paraffin embedded tissues and frozen sections.

In yet another embodiment of the present invention, a method of detecting a cancerous cell in a biological sample having the above-described characteristics uses a microscope being capable of detecting, measuring and calculating UV absorption signals and optionally phase-contrast signals. In a preferred embodiment, one will use a confocal laser scanning microscope.

In all of the aforementioned methods, one may rely on (UV) light with a predetermined single wavelength for detecting the nucleus and measuring nuclear UV absorbance.

In another embodiment of the present invention, an in vitro method of diagnosing and/or predicting cancer in a human or animal subject is provided which comprises steps of:
a) providing a biological sample from the subject;
b) determining the position and/or dimensions of the nucleus within at least one cell of said sample in vitro,
c) measuring in vitro the UV absorbance within the nucleus' boundaries as determined in a),
d) calculating from the nuclear signal intensity obtained in step d) the ploidy state of said at least one cell, and
e) deciding on the presence and/or likely future occurrence of a cancer depending the ploidy state.

The methods of diagnosis in accordance with the present invention also comprise various embodiments which realize the basic concept of determining the position and/or dimensions of the nucleus within a cell and determining the UV absorbance within the nucleus' boundaries. For determining the nucleus position and/or dimensions which is equivalent to determining the nucleus' boundaries one can again use phase contrast microscopy with visible light as well as detection approaches with UV light. For determining the UV absorbance of the nucleus one may rely solely on UV measurements without adding fluorescent markers that are capable of interacting with double stranded nucleic acids or one may use such markers.

While the methods of diagnosis will again mainly be described with respect to two exemplary embodiments, i.e. localizing the cell nucleus with phase contrast microscopy and determining UV absorbance of the nucleus using the above described markers, or using UV absorbance measurements for localizing the nucleus and measuring nuclear UV absorbance without the above described markers, the skilled person will understand that, if certain aspects such as preferred wavelengths, the nature of the markers, the detection devices to be used etc., are discussed in the context of these two embodiments, these explanations equally apply two the other embodiments of the invention as mentioned above unless it is explicitly indicated otherwise. The definition of terms such as "cell", "cancerous cell", "sample", "aneuploidity" etc., of course, have the same meaning throughout these various embodiments of the invention unless indicated otherwise.

Of course, aspects described above such as using certain wavelengths or certain types of microscopes etc. equally apply in the context of diagnosis.

Thus, in one exemplary embodiment, the position and/or dimensions of the nucleus may be (roughly) determined in said at least one cell by using UV light and/or phase-contrast microscopy. If UV light is used in step b), one will preferably use UV light of a wavelength between approximately 240 nm and approximately 280 nm. Particularly preferred are wavelengths such as approximately 250 nm, 255 nm or 260 nm.

In yet another embodiment of the present invention, in step b) the position and/or dimensions of the nucleus within said at least one cell is determined by phase-contrast microscopy solely.

In another exemplary embodiment, one uses UV light of a wavelength between approximately 240 nm and approximately 280 nm for measuring UV absorbance in step c). Particularly preferred are wavelengths such as approximately 250 nm, 255 nm or 260 nm.

In yet another embodiment one can contact said at least one cell with at least one fluorescent marker which is capable of interacting with double stranded nucleic acids within said at least one cell and then determines the nuclear signal intensity of said at least one fluorescent marker being bound to nuclear double stranded nucleic acids in step c). To this end, one can use UV light with a wavelength between approximately 240 nm and approximately 280 nm.

In another exemplary embodiment of the method of diagnosis, it is not necessary to visualize the nuclear nucleic acids such as DNA of said cell by e.g. immuno-histochemical stains, chemical reactions such as the Feulgen reaction or fluorescent markers.

If fluorescent markers are to used, the same kind of markers as described above and hereinafter may be contacted with the cell(s).

Yet another embodiment of this aspect of the invention relates to an in vitro method of diagnosing and/or predicting cancer in a human or animal subject with the method comprising the above-mentioned characteristics and wherein a ploidity state deviating by at least 10% from 2n or 4n with n being the number of chromosomes is indicative of a cancerous cell and thus on the presence or likely development of (future) cancer.

Of course, for these aspects of the invention that are concerned with methods of diagnosis, the biological samples may be selected from the same samples as described above.

Accordingly, the cancers, which are diagnosed and/or predicted by the described methods of diagnosis, may be selected from the same group of cancers as described above.

In yet another embodiment of the present invention, the method for diagnosing and/or predicting cancer in a human or animal subject uses a microscope that is capable of detecting UV absorption signals, fluorescent signals and wich may optionally be employed for phase-contrast purposes. For determining the position and/or dimensions of the nucleus and nuclear UV absorption it can be preferred to use a confocal laser-scanning microscope.

DETAILED DESCRIPTION OF THE INVENTION

Figure 1:
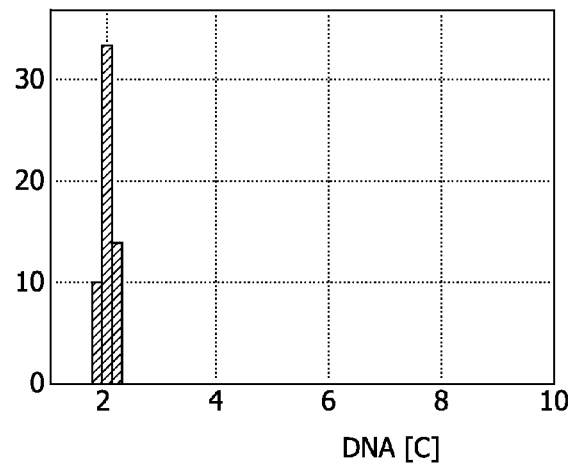
FIG. 1 shows a histogram, i.e. a densitometric profile as typically obtained if nuclear DNA content of a population of non-cancerous cells is determined. The cells are in a non-proliferative state.

Identification of cancerous cells by DNA cytometry is typically carried out using flow cytometry or image cytometry.

In the case of DNA image cytometry which may also be designated as ICM, DNA is stained with a marker in order to visualize the DNA. Subsequently, alterations in the amount of the DNA or structural chromosomal aberrations which are commonly designated as aneuploidy are used to detect the presence of a cancerous cell as aneuploidy is considered to be characteristic of either an already existing cancerous state or a developing transitional cancerous state. Thus, detection of DNA aneuploidy allows an early and sensitive diagnosis of cancer by detecting cancerous cells, often years ahead of morphological and histological characterization of tissue biopsies.

However, as mentioned above established DNA colouring reactions such as the Feulgen staining method are laborious and time-consuming.

The inventors have surprisingly found that neither immunohistochemical stainings nor fluorescent markers or chemical reactions are necessary in order to determine in vitro the amount of nuclear DNA and thus the ploidy state of a cell.

Instead, the investors have found that, once one has determined the position and/or dimensions/boundaries of the nucleus within a cell, one can solely rely on UV light to determine the UV absorbance by the nucleus. The determined UV absorbance can then be used to calculate the nuclear DNA content or ploidy state of a cell. These findings particularly apply if one uses UV light with a preferred wavelength between approximately 240 nm and approximately 280 nm.

The inventors have further surprisingly found that one can also use fluorescent markers which are capable of specifically interacting with double stranded nucleic acids within a cell in DNA image cytometry based methods of detecting cancerous cells in a biological sample.

Thus, the present invention in one embodiment is directed to a method of determining in vitro the amount of nuclear nucleic acids in at least one cell being present in at least one biological sample comprising the steps of:
a) determining the position and/or dimensions of the nucleus within said cell in vitro,
b) measuring in vitro the UV absorbance within the nucleus' boundaries as determined in a).

As outlined above, basically any method may be used in step a) which allows determination of the position and/or dimensions and thus the boundaries of the nucleus. One such example is phase contrast microscopy. However, it can be preferred to use only ultraviolet (UV) light in step a) of a preferred wavelength between approximately 240 nm and approximately 280 nm. Particularly preferred wavelengths in step a) and b) are approximately 250 nm, 255 nm or 260 nm.

If one uses phase contrast microscopy, it can be preferred to determine nuclear UV absorbance, i.e. nuclear signal intensity by contacting the cell(s) with one of the above or below mentioned fluorescent markers.

However, in other exemplary embodiments of the present invention, it is not necessary to assist visualization of nuclear nucleic acids by contacting cells with fluorescent markers.

Such methods can be used inter alia to determine the genome size of an individual or species. Of course, such methods can also be used to detect at least one cancerous cell within at least one biological sample. Comparing the nuclear UV absorption obtained with the nuclear UV absorption of non-cancerous cells, which has been analyzed using the same approach, may do this.

As laid out above, the methods of the present invention comprises various embodiments which realize the basic concept of determining the position and/or dimensions of the nucleus within a cell and determining the UV absorbance within the nucleus' boundaries. For determining the nucleus position and/or dimensions which is equivalent to determining the nucleus' boundaries one can use phase contrast microscopy with visible light as well as detection approaches with UV light. For determining the UV absorbance of the nucleus one may rely solely on UV measurements without adding fluorescent markers that are capable of interacting with double stranded nucleic acids or one may use such markers.

Thus, one can in principle localize the cell nucleus with phase contrast microscopy and determine UV absorbance of the nucleus without using the above described markers, one can localize the cell nucleus with phase contrast microscopy and determine UV absorbance of the nucleus using the above described markers, one can use UV absorbance measurements for localizing the nucleus and measuring nuclear UV absorbance without the above described markers, and one can use UV absorbance measurements for localizing the nucleus and measuring nuclear UV absorbance with the above described markers, etc.

The invention in two of its exemplary embodiments is concerned with localizing the cell nucleus with phase contrast microscopy and determining UV absorbance of the nucleus using the above described markers, or using UV absorbance measurements for localizing the nucleus and measuring nuclear UV absorbance without the above described markers. These two embodiments will be described in further detail hereinafter. However, the skilled person is clearly aware that if certain aspects such as preferred wavelengths, the nature of the markers, the detection devices to be used etc., are discussed in the context of these two embodiments that these explanations equally apply two the other embodiments of the invention as mentioned above unless it is explicitly indicated otherwise. The definition of terms such as "cell", "cancerous cell", "sample", "aneuploidy" etc., of course, have the same meaning throughout the various embodiments of the invention unless indicated otherwise. The various methods as envisaged by the present invention can also be used for the same purposes.

Before some of the embodiments of the present invention are described in more detail, the following definitions are introduced.

As used in this specification and in the appended claims, the singular forms of "a" and "an" also include the respective plurals unless the context clearly dictates otherwise. Thus, the term "a microcarrier bead" can include more than one microcarrier bead, namely two, three, four, five etc. microcarrier beads.

The terms "about" and "approximately" in the context of the present invention denotes an interval of accuracy that the person skilled in the art will understand to still ensure the technical effect of the feature in question. The term typically indicates a deviation from the indicated numerical value of +/−10%, and preferably +/−5%. The term "approximately" in the context of wavelength relates to deviations of 1.5%, preferably 1% and most preferably of 0.5%.

For the purposes of the present invention the term "in vitro" refers to analysis of cells, which have been isolated from their natural environment and are investigated outside the human or animal body.

For the purposes of the present invention the term "cancerous cell" relates to any cell, cellular tissue or organ made of cells with some or all of the cells comprising an amount of nuclear DNA which deviates from the amount of nuclear DNA as determined for a non-cancerous cell as a consequence of chromosomal duplications, deletions, insertions, translocations, etc.

It is well-known that insertions, duplications, deletions and translocations of chromosomal DNA are to a large extent responsible for the development of cancer and can thus be considered to be characteristic of cancerous cells.

For the purposes of the present invention, the term "biological sample" relates to any sample comprising cellular matter and preferably cells of a human or animal subjects which are to be tested for the amount of nuclear DNA in these cells and particularly the presence of cancerous cells.

Such biological samples may thus be selected from the group comprising bone marrow cells, lymph node cells, lymphocytes, erythrocytes, neural cells, muscle cells, fibroblasts, keratinocytes, mucosal samples, peripheral blood samples, cerebrospinal fluid samples, urine samples, effusion samples, fine needle aspirates, fine needle aspiration biopsies, brush biopsies, peripheral blood scrapings, skin scrapings, smears from exfoliated cells, cytocentrifuged preparations from body fluids, cell separation specimen (after mechanic and/or enzymatic dispersions), paraffin embedded tissues and frozen sections.

The term "nuclear signal intensity" is typically used in the context of using fluorescent markers and explained further below. The person skilled in the art will understand that the nuclear signal intensity is correlated with nuclear UV absorbance given that the signal intensity will usually be the higher the more UV light is absorbed by the fluorescent markers that are localized to the nucleus.

For the purposes of the present invention the term "fluorescent marker" refers to any molecule which is capable of specifically interacting with double stranded nucleic acids and which provides a fluorescent signal upon excitation with a suitable light source. In general, fluorescent markers in accordance with the invention will absorb light of a wavelength between approximately 100 nm (UV) to approximately 800 nm.

Such fluorescent markers may bind e.g. to the major or minor DNA grooves. They may be nucleic acid base-intercalating agents and can be selected from the group comprising 4',6'-diamidino-2-phenylindole (DAPI), Propidium Iodide (PI) and Ethidium bromide (EtBr). Fluorescent markers also include SYBR green.

Other fluorescent agents comprise SYTOX Blue, SYTOX Green, SYTOX Orange, POP-1, BOBO-1, YOYO-1, TOTO-1, JOJO-1, POPO-2, LOLO-1, BOBO-1, YOYO-3, TOTO-3, PO-PRO-1, BO-PRO-1, TO-PRO-1, JO-PRO-1, PO-PRO-3, LO-PRO-1, BO-PRO-3, YO-PRO-3, TO-PRO-3, TO-PRO-5, SYTO 40 blue-fluorescent nucleic acid stain, SYTO 41 blue-fluorescent nucleic acid stain, SYTO 42 blue-fluorescent nucleic acid stain, SYTO 43 blue-fluorescent nucleic acid stain, SYTO 44 blue-fluorescent nucleic acid stain, SYTO 45 blue-fluorescent nucleic acid stain, SYTO 9 green-fluorescent nucleic acid stain, SYTO 10 green-fluorescent nucleic acid stain, SYTO 11 green-fluorescent nucleic acid stain, SYTO 12 green-fluorescent nucleic acid stain, SYTO 13 green-fluorescent nucleic acid stain, SYTO 14 green-fluorescent nucleic acid stain, SYTO 15 green-fluorescent nucleic acid stain, SYTO 16 green-fluorescent nucleic acid stain, SYTO 20 green-fluorescent nucleic acid stain, SYTO 21 green-fluorescent nucleic acid stain, SYTO 22 green-fluorescent nucleic acid stain, SYTO 23 green-fluorescent nucleic acid stain, SYTO 24 green-fluorescent nucleic acid stain, SYTO 25 green-fluorescent nucleic acid stain, SYTO 26 green-fluorescent nucleic acid stain, SYTO 27 green-fluorescent nucleic acid stain, SYTO BC green-fluorescent nucleic acid stain, SYTO 80 orange-fluorescent nucleic acid stain, SYTO 81 orange-fluorescent nucleic acid stain, SYTO 82 orange-fluorescent nucleic acid stain, SYTO 83 orange-fluorescent nucleic acid stain, SYTO 84 orange-fluorescent nucleic acid stain, SYTO 85 orange-fluorescent nucleic acid stain, SYTO 86 orange-fluorescent nucleic acid stain, SYTO 17 red-fluorescent nucleic acid stain, SYTO 59 red-fluorescent nucleic acid stain, SYTO 61 red-fluorescent nucleic acid stain, SYTO 17 red-fluorescent nucleic acid stain, SYTO 62 red-fluorescent nucleic acid stain, SYTO 63 red-fluorescent nucleic acid stain, SYTO 64 red-fluorescent nucleic acid stain, Acridine homodimer, Acridine orange, 7-AAD (7-amino-actinomycin D), Actinomycin D, ACMA, DAPI, Dihydroethidium, Ethidium Bromide, Ethidium homodimer-1 (EthD-1), Ethidium homodimer-2 (EthD-2), Ethidium monoazide, Hexidium iodide, Hoechst 33258 (bisbenzimide), Hoechst 33342, Hoechst 34580, Hydroxystibamidine, LDS 751 or Nuclear yellow. All these compounds are available e.g. from Invitrogen GmbH, Germany.

For the purposes of the present invention, the term "interacting with double stranded nucleic acids" refers to the capability at the at least one fluorescent marker to interact with nucleic acids that have a double stranded confirmation.

The fluorescent markers may in one preferred embodiment interact specifically with double stranded nucleic acids. In this context the term "specifically interacting with double stranded nucleic acids" refers to the capability at the at least fluorescent marker to interact preferentially with nucleic acids that have a double stranded confirmation.

Preferential binding refers to the capability of the fluorescent markers to interact under identical conditions with double stranded nucleic acids, but not with single stranded nucleic acids or at least to a lesser degree.

Whether a fluorescent marker does interact preferentially with a double stranded nucleic acid and not with a single stranded nucleic acid may be determined by in vitro experiments in which an immobilized isolated double stranded nucleic acid and an immobilized isolated single nucleic acid are contacted in parallel under identical conditions and incubated at room temperature. Afterwards, a washing buffer is applied. If, for the double stranded nucleic acid, after excitation with a suitable light source emitting a wavelength as mentioned above, a signal is observed which is stronger than for the single stranded nucleic acid, the fluorescent marker is considered to be specific for double stranded nucleic acids.

In another embodiment, the fluorescent markers may not be specific for double stranded nucleic acids as defined above, but have the capability of giving a stronger fluorescent signal when bound to nucleic acids compared to when they are not bound.

In case of Ethidium Bromide for example, the fluorescent signal increase ~20 fold when bound to double stranded nucleic acids and ~10 fold when bound to single stranded molecules. For SYBR green I, the fluorescent signal increases ~200 fold when bound to double stranded DNA. It is thus not absolutely necessary to have a marker which is specific for double stranded nucleic acids because according to the invention, one discriminates between nuclear and cytoplasmic staining as will be explained below. If one uses a marker that yields brighter signals when bound to DNA, one can potentially avoid washing as will be explained hereinafter.

Of course, in a preferred embodiment one may use markers such as e.g. Ethidium Bromide which interacts specifically with double stranded nucleic acids and have the capability of giving stronger signals in the bound vs. non-bound state.

Before determining the position and/or dimensions, i.e. the boundaries of the nucleus of a cell, and also before the at least one (putatively cancerous) cell in the at least one biological sample is contacted with the at least one fluorescent marker being capable of specifically interacting with double stranded nucleic acids, it may be necessary and/or advisable for some embodiments of the present invention to prepare the biological sample such that the at least one (putatively cancerous) cell is prepared for measuring UV absorbance.

Preparing biological samples for testing of cells within a biological sample in DNA image cytometry is well-known by the person skilled in the art and may include dilution of the samples, isolation of homogeneous cell populations by fluorescence activated cell sorting (FACS), enrichment and purification of certain cell types such as bone marrow cells, lymph node cells, lymphocytes, red blood cells, liver cells, renal cells, neural cells, fibroblasts, keratinocytes etc. using immunoenrichment or classical cell biology and biochemical techniques including enzymatic hydrolysis, mechanical or osmotic rupture, (density) centrifugation, chromatography, buffer dialysis, etc.

If necessary, the cellular samples that are immobilized on a solid substrate can be fixed. In this context, the person skilled in the art will consider typical fixation aids such as drying, formaldehyde, paraformaldehyde, ethanol, propanol, methanol-acetone, methanol-glacial acetic acid, methanol-formalin-glacial acetic acid etc.

While fixing may be useful in some case, it is not always necessary. If the sample is examined using an integrated device, it may be recommendable to not fix the cells and to only immobilise them If, however, fixing is considered, one may proceed according to standard protocols, which comprise e.g. the steps of:
in case of paraformaldehyde:
add 4% PF solution in PBS to cells
incubate 5-30 min at room temp
wash with PBS
in case of Methanol/Acetone:
put substrate with cell in ice cold 100% Methanol
incubate 5-30 min at −20° C.
rinse substrate with cells with 100% acetone
let acetone evaporate).

Protocols which may be used for the above described activities, i.e. the isolation and preparation of the sample, the isolation and preparation of cells, the immobilization, permeabilization and fixation of cells may e.g. be taken from standard cell biology text books and laboratory manuals on e.g. fluorescence microscopy such as Cell Biology: A laboratory handbook, Volumes I-III, Cellis, J. E. ed. (1994); Ausubel et al., Current Protocols in Molecular Biology, Volumes I-III, Ausubel, R. M. ed. (1994), etc.

One may then proceed to step a) in order to determine the position and/or dimensions of the nucleus within said cell using e.g. ultraviolet (UV) light of a preferred wavelength between approximately 240 nm and approximately 280 nm or e.g. using phase contrast microscopy.

In the following, two exemplary embodiments of the invention will be discussed in greater detail. In the first embodiment, which will hereinafter be designated as Embodiment 1, localization of the nucleus and determination of nuclear UV absorbance is performed using UV light of a preferred wavelength and preferably does not involve phase contrast microscopy and/or the use of fluorescent markers. In the second embodiment, which will hereinafter be designated as Embodiment 2, localization of the nucleus and determination of nuclear UV absorbance is performed using phase contrast microscopy and fluorescent markers. The skilled person understands that certain aspects of these two embodiments which will be discussed in closer detail such as the incubation and washing steps in case that fluorescent markers are used, the detection devices and UV wavelength ranges can nevertheless similarly applied to other of the embodiments envisaged above. After some of the issues of the two embodiments have been described, it will then be discussed how the nuclear UV absorbance/nuclear signal intensities can be used to determine the ploidy state of cells and thus the presence and/or likely occurrence of cancerogenic properties.

Embodiment 1—Determination of Amount of Nucleic Acids

As mentioned, the present invention in one embodiment is directed to a method of determining in vitro the amount of nuclear nucleic acids in at least one cell being present in at least one biological sample comprising the steps of:
  a) determining in vitro the position and/or dimensions of the nucleus within said cell;
  b) determining in vitro the UV absorbance within the nucleus' boundaries as determined in a) using UV light of a preferred wavelength between approximately 240 nm and approximately 280 nm.

However, in a preferred embodiment one will use ultraviolet (UV) light of a preferred wavelength between approximately 240 nm and approximately 280 nm. Particularly preferred wavelengths in step a) and b) are approximately 250 nm, 255 nm or 260 nm.

The above-specified method of determining the amount of a nuclear nucleic acid, which preferably is used for detection of at least one cancerous cell in at least one biological sample, will now be described in more detail with respect to the single steps a) to b).

Once one has prepared the cell(s) as described above one may then proceed to step a) in order to determine the position and/or dimensions of the nucleus within said cell using ultraviolet (UV) light of a preferred wavelength between approximately 240 nm and approximately 280 nm.

Figure 4:
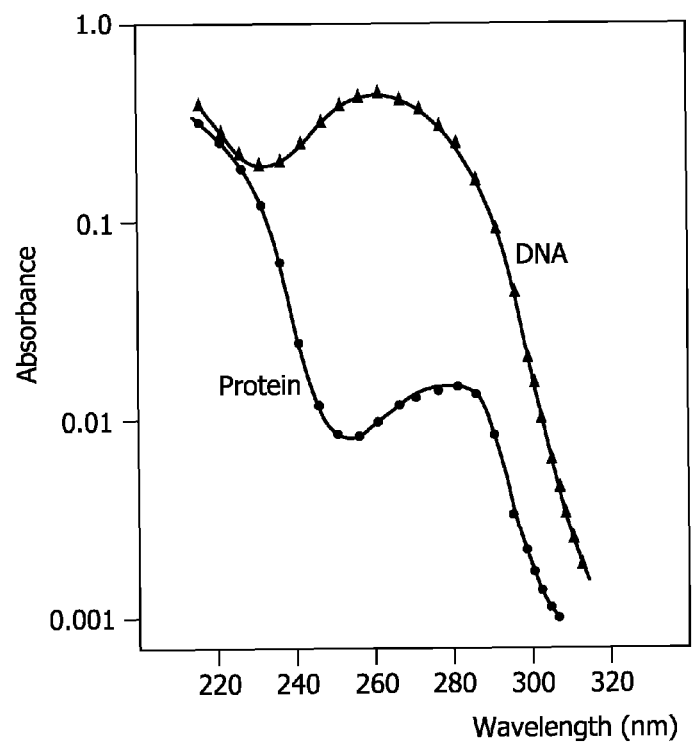
FIG. 4 shows the different absorption behavior of DNA and protein in the range between approximately 230 nm and 300 nm wavelength.

DNA absorbs UV light between wavelength of 230 to 290 nm with different efficiency compared to proteins. In FIG. 4, the absorption in this wavelength area for proteins and DNA is plotted as a function of wavelength. From this one clearly can see that when using UV light of a wavelength of approximately 240 nm to 280 nm, such as 250 nm, DNA absorbs much more (approximately 50 times more) light than proteins.

This behaviour can be used to determine the boundaries, i.e. the position and/or dimension of a cell nucleus.

One can for example use a light spot emitting light between approximately 240 nm and approximately 280 nm and scan with this light spot through a cell within one plane of the cell. This may e.g. be done with a confocal laser scanning microscope. As the nucleus comprises almost all DNA of a cell and as the cytoplasm largely consists of proteins, one will observe a sharp increase in absorption once the light spot traverses from the cell cytoplasm to the cell nucleus. If thus a plane section of a cell is scanned with such a light spot, one can clearly identify the boundaries of the cells nucleus by measuring the change in absorption.

For the purposes of the present invention the boundaries of a nucleus within a cell can thus be determined using UV light of a preferred wavelength between approximately 240 nm and approximately 280 nm. In further preferred embodiments of the invention, the wavelength is approximately 250 nm, 255 nm or 260 nm.

Using a confocal microscope set-up one can focus a probe being inside the nucleus of the cell. Typically one will let the probe spot of the confocal set-up be smaller than the nucleus.

Using this approach one can not only locate the position of the nucleus within a single frame but actually can determine the overall dimensions of the nucleus, i.e. its volume.

This can be done as follows. By scanning a light spot in a single plane as described one can determine the intensity of the reflected light as described. The distance in the direction of movement over which the signal is comparatively low measures the local thickness of the nucleus.

Figure 5:
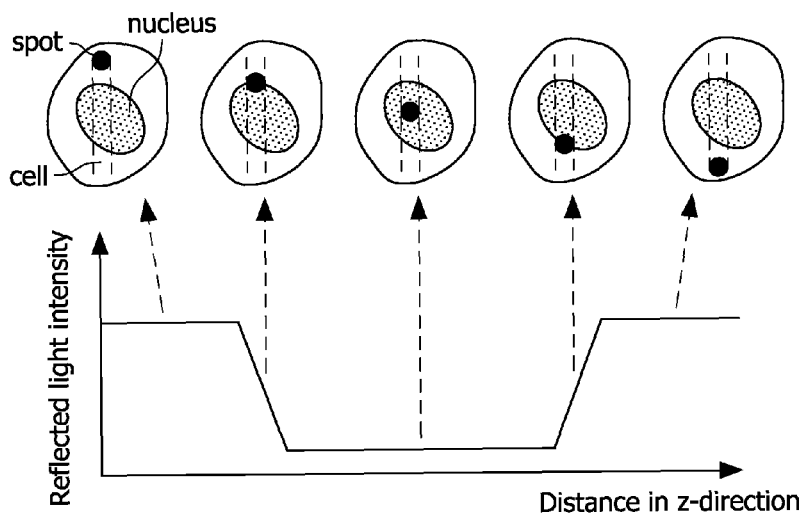
FIG. 5 shows shows schematically the principle of one embodiment of the present invention for determining the boundaries of a cell nucleus using UV light of a wavelength between approximately 240 nm and approximately 280 nm.

As FIG. 5 illustrates for a single scan within a single plane of the nucleus, these 1-D scans can be extended to 3 dimensions to obtain the full shape of the nucleus by performing the same measurement for different planes. At different coordinates (xy) the local thickness of the nucleus is measured in the z-direction. Thus, by reconstructing a 3-D image from the different 1-D images of various planes one can reconstruct and calculate the appearance and volume of the nucleus.

The amount of UV light reflected back from the nucleus as measured by the confocal set-up is inversely related to the amount of light absorbed by the area probed by the spot. Assuming that absorption is almost equal throughout the nucleus, one can then preferably calibrate the measurement and determine UV absorption of nuclear nucleic acids.

Calibration consists of determining absorption of UV light by a nucleus and by the regions outside the nucleus within the same plane of the confocal scan. For both measurements in and outside the nucleus, the light has travelled almost through the same amount and distance of tissue before reaching the cell of interest resulting in comparable and similar background signals in both measurements. Therefore, the ratio between the measurements for nuclear absorptions versus non-nuclear absorption can be taken as an absolute measurement for absorption of the cell nucleus. However, if monolayer of cells are analysed it may not always be necessary to calibrate the signal.

In the preferred embodiment of the invention one will use UV light of a wavelength between approximately 240 nm and approximately 280 nm. In a particularly preferred embodiment one will use UV light with a wavelength of 250 nm, 255 nm or 260 nm.

The reason for using UV light and particularly UV light of a wavelength between 240 nm and 280 nm is again that DNA which is found in the nuclei of cells shows a much higher absorption in this wavelength range than for proteins of (see FIG. 4).

The nucleus, containing both proteins and DNA will therefore absorb more light than the rest of the cell, which contains mainly proteins, but rather no DNA.

Using preferably a confocal laser scanning microscope one can measure the reflection of UV light by material inside the nucleus and compare it to the reflection by the cell material outside the nucleus. By calculating the ratio of UV light absorbed by the nucleus to UV light absorbed by the regions outside the nucleus, one obtains thus a signal that is a measurement for the density of DNA within a single plane as obtained with a confocal scan.

Thus, measurement of nuclear UV absorbance is, according to the invention, obtainable by inter alia calibrating the UV absorbance signal in the nucleus. The (calibrated) signal of a single plane may be taken as measurement of UV absorption if only signals of the same plane are compared. One may, however, also sum up the (calibrated) signals of the various planes that have been used for determination of the volume of the nucleus (see above) and thus obtain a measure for UV absorption of the whole nucleus.

All this is preferably done using confocal laser scanning microscopy with UV light of a wavelength between approximately 240 nm and between approximately 280 nm. In a particularly preferred embodiment, one uses UV light of approximately 250 nm, 255 nm or 260 nm.

The person skilled in the art is of course well-acquainted with methods of recording UV absorbance signals as well as using these signals to calculate images of the e.g. cell nucleus.

Determination of signal intensities, i.e. the amount of absorbed or transmitted light, will be done using instruments as typically used for these purposes.

For detection of the signals one may use a microscope that is capable of detecting UV absorption signals. In a preferred embodiment of the invention, the same microscope may provide the required devices to view the cell(s) to be examined also in phase contrast. One microscope type that may preferably be used to detect the UV absorption signal may be a confocal laser scanning microscope.

Confocal microscopy offers several advantages over conventional optical microscopy, one of the most important being the elimination of out-of-focus information that distorts the image, controllable depth of field and sub-micron resolution. A further advantage of confocal microscopy is that fluorescence of various portions of the specimen that are out-of-focus can be filtered out and so do not interfere with the portions or sections that are in-focus thereby yielding an image that is considerably sharper and shows a better resolution than a comparable image obtained by classical light microscopy.

The basic principle of confocal scanning microscopy is the use of a screen with a pinhole at the focal point of the microscope lens system which is "conjugate" to the point at which the objective lens is focussed. Only light coming from the focal point of the objective is focussed at the pinhole and can pass through to the detector, which e.g. may be a charge coupled device (CCD). Light coming from an out-of-focus section of the sample will be nearly completely filtered out.

Thus, a confocal microscope has a significantly better resolution than a conventional microscope for the x- and y- direction. Furthermore, it has a smaller depth of field in the z-direction. By scanning the focal point through the sample, it is thus possible to view different planes of a sample and to then rebuild a 3-dimensional image of the sample. Furthermore, confocal microscopy is compatible with different wavelengths of light.

For localisation of the nucleus the confocal scanning microscope may use monochromatic or polychromatic light; however, monochromatic UV light with a wavelength between 240 nm and 280 nm may be preferred. Particularly preferred may be UV light of a wavelength of 250 nm, 255 nm or 260 nm.

As a confocal laser scanning microscope one may use a microscope such as LEICA DMLM and having a Qimaging Retiga 2000R FASTCooled Mono 12-bit camera unit (www.qimaging.com) for measuring the signal intensity of the fluorescence signal.

Determination of signal intensities, i.e. the amount of absorbed or transmitted light, will be done using instruments as typically used for these purposes.

Thus, one may e.g. use a charge-coupled device or a digital camera being linked to the microscope aperture that is used for viewing the cells when excitated with the above-mentioned light sources. One may of course also use films etc.

Detection units may e.g. be Optronics DEI-700 CE three-chip CCD camera connected via a BQ6000 frame-grabber board to computer. Alternatively one may use a Hitachi HV-C20 three-chip CCD camera. Software packages for image analysis may e.g. be the Bioquant True Color Windows 98 v3.50.6 image analysis software package (R&M Biometrics, Nashville, Tenn.) or Image-Pro Plus 3.0 image analysis software. Another system that may be used is the BioView Duet system (BioView Ltd, Rehovot, Israel which is based on a dual mode, fully automated microscope (Axioplan 2, Carl Zeiss, Jena, Germany), an XY motorized 8-slides stage (Marzhauser, Wetzler, Germany) a 3CCD progressive scan color camera (DXC9000, Sony, Tokyo, Japan) and a computer for control and analysis of the system and the data.

One of the advantages of the present invention is that the determination of the boundaries of the cell nucleus and measurement of nuclear UV absorption is done with the same instrument such as a confocal laser scanning microscope.

Another advantage is that the present invention does not require visualizing of the nuclear DNA with e.g. fluorescent markers (although these may be used), chemical reactions or immunohistochemical stainings as the preferred UV wavelength of 240 nm to 280 nm and particularly 250 nm, 255 nm and/or 260 nm is sufficient to reliably identify the nucleus and the UV absorption values which can be used to calculate the amount of nuclear DNA present.

Embodiment 2—Determination of Amount of Nucleic Acids

As mentioned, the present invention in one embodiment is directed to a method of determining in vitro the amount of nuclear nucleic acids in at least one cell being present in at least one biological sample comprising the steps of:
  a) contacting said at least one cell with at least one fluorescent marker which is capable of interacting with double stranded nucleic acids within said at least one cell;
  b) determining the signal intensity of said at least one fluorescent marker being bound to double stranded nucleic acids with the signal being obtained by excitation with a suitable light source;
  c) determining the position and/or dimensions of the nucleus within said at least one cell by phase-contrast microscopy;
  d) determining the nuclear signal intensity of fluorescent marker being bound to nuclear double stranded nucleic acids by correlating the signal intensity obtained in b) with the position and/or dimensions of the nucleus obtained in c).

In an alternative embodiment of the invention, step c) may proceed step a) and step d) may follow step b).

Once the cells including the at least one (putatively cancerous) cell of the at least one biological sample to be examined have been prepared in a suitable manner, the immobilized and optionally permeabilized and fixed cells may be contacted with the at least one fluorescent marker being capable of specifically interacting with double stranded nucleic acids within cells.

For this purpose, the at least one fluorescent markers may be formulated in a suitable incubation buffer. In principle any isotonic buffer of neutral pH can be used.

The cellular samples may be incubated with such a fluorescent marker containing solution for at least 10 seconds) at a temperature of at least 4° C. Typically and in some instances preferably, incubation will be performed for several minutes at room temp (e.g 20-25° C.).

Once one has contacted the at least one (putatively cancerous) cell of the cellular sample as obtained from the at least one biological sample with the at least one fluorescent marker which is capable of specifically interacting with double stranded nucleic acids, one determines in a second step which has been designated above as step b) the signal intensity of said at least one fluorescent marker being specifically bound to double stranded nucleic acids within the incubated cells as obtained by excitation with a suitable light source.

Before the signal intensity is measured, one may optionally wash the cellular sample that has been incubated with the fluorescent marker containing incubation solution in order to enhance the signal to background ratio of the signal. Such washing solutions may comprise buffers with physiological higher salt concentrations or and/or detergents such as NP-40, Tween 20, Tween 80, Triton X100 etc. in order to reduce non-specific interactions and background signals. Such a washing buffer may comprise e.g. PBS pH 7.4 with 0.05% Tween20. Any istonic buffer of physiological pH may be used. The washing step is optional as the fluorescent markers show increased signal strength when bound to double stranded nucleic acids versus the non-bound markers. However, for an improved signal to background ratio a washing step may be preferred.

Excitation will be performed with a light source that is capable of exciting the fluorescent marker. In general, the light source will emit a wavelength between approximately 100 nm to approximately 800 nm. The excitation wavelength will depend on the nature of the fluorescent marker being used. In the case of Ethidium bromide, Propidium-Iodide and DAPI one will typically use ultraviolet light ranging from approximately 300 nm to approximately 550 nm. This later wavelength range may also be preferred for other markers such as Propidium Iodide etc.

Depending on the absorption spectrum of the fluorescent markers being used, the light source may emit monochromatic or polychromatic light.

It is to be understood that the signal intensity of the fluorescent marker is measured for different cells individually which makes it necessary that a microscope is used in order to allow spatial separation of the cells.

For detection of the signal one may use a microscope that is capable of detecting fluorescent signals. In a preferred embodiment of the invention, the same microscope may provide the required devices to view the cell(s) to be examined also in phase contrast. One microscope type that may be used to detect the fluorescence signal may be a confocal laser scanning microscope. However, for the applications which are typically envisaged for the inventive methods, a phase contrast microscope which is equipped with required filters, detection units, software etc. may be sufficient.

Determination of signal intensities, i.e. the amount absorbed or transmitted light, will be done using instruments as typically used for these purposes. Some of these instruments have already been described above in the context of Embodiment 1.

Thus, one may e.g. use also a charge coupled device or a digital camera being linked to the microscope aperture that is used for viewing the cells when excitated with the abovementioned light sources. One may of course also use films etc.

Fluorescence measurements can again be made with any standard filter cube (consisting of a barrier filter, excitation filter and the dichroic mirror) or any customized filter cube for special applications provided that the emission spectrum is within the spectral range of the system sensitivity. Spectral bioimaging can also be used in conjunction with any standard spatial filtering methods such as dark field and phase-contrast and even with polarized light microscopy.

Fluorescence-optical read-outs of signals generated by the fluorescent markers can be recorded, as stated above, using e.g. charge coupled devices (CCD) which for the purpose of qualitative differentiation of optical effects (scattering, reflection) achieve excitation of the fluorophores and the dark field (by way of reflected-light microscopy or transmitted-light microscopy). In this process imaging of the cells takes place either by exposure or by restoring with the use of high resolution optics. Confocal scanning systems such as described in U.S. Pat. No. 5,304,810 make it also possible to evaluate fluorescence signals from selected planes of a sample. They are based on selecting the fluorescence signals along the optical axis by means of pinholes and are often equipped with a powerful autofocus system. Such systems allow to precisely locate signals originating from fluorescent markers and to measure their signal intensities.

Detection units may again e.g. be Optronics DEI-700 CE three-chip CCD camera connected via a BQ6000 frame-grabber board to computer. Alternatively one may use a Hitachu HV-C20 three-chip CCD camera. Software packages for image analysis may e.g. be the Bioquant True Color Windows 98 v3.50.6 image analysis software package (R&M Biometrics, Nashville, Tenn.) or Image-Pro Plus 3.0 image analysis software. Another system that may be used is the BioView Duet system (BioView Ltd, Rehovot, Israel which is based on a dual mode, fully automated microscope (Axioplan 2, Carl Zeiss, Jena, Germany), an XY motorized 8-slides stage (Marzhauser, Wetzler, Germany) a 3CCD progressive scan color camera (DXC9000, Sony, Tokyo, Japan) and a computer for control and analysis of the system and the data.

One may thus also use a microscope such as LEICA DMLM with phase contrast and having a Qimaging Retiga 2000R FASTCooled Mono 12-bit camera unit (www.qimaging.com) for measuring the signal intensity of the fluorescence signal.

As it is well-known that detection units for measuring signal intensity of fluorescence signals can reach a saturation limit it may be necessary to dilute the fluorescent marker solutions which are used for contacting the cellular samples with the fluorescent markers and/or to dilute the cellular samples correspondingly.

In a third step which has been designated above as step c) the position and/or dimensions of the nucleus of the cells of the biological sample including the at least one (putative cancerous) cell are determined using phase-contrast microscopy. For this purpose, a typical microscope such as a LEICA DMLM with phase contrast may be used.

A person skilled in the art is well acquainted with the microscopic analysis of fixed and immobilized cells by phase-contrast microscopy.

For the purposes of the present invention, it may be desirable that a microscope will be used that allows to detect signals generated by the fluorescent marker and at the same time allows viewing of the same cells and thus determination of the position and/or dimensions of the nucleus by phase-contrast microscopy. In this case, confocal laser scanning microscope such as the aforementioned microscopes may be used. Microscopes which at the same time allow to record fluorescent signals and phase-contrast pictures include inter alia microscope such as LEICA DMLM with NPlan 20×/0.40 PH1 objective or Nplan 40×/0.65 PH2 objective. However, detection of fluorescent signals and determination of the position and/or dimensions of the cell nucleus by phase contrast microscopy may also be performed using different devices.

Once one has determined the signal intensity of the fluorescent marker after excitation with a suitable light source and determined the position and/or dimensions of the nucleus of the observed cells in the sample, in a fourth step which has been designated above as step d), one can determine the nuclear signal intensity of the fluorescent marker being specifically bound to double stranded nucleic acids and preferably nuclear DNA by correlating the signal intensity obtained in aforementioned step b) with the position and/or dimensions of the nucleus obtained in aforementioned step c) of the above-described method. This step is required as one typically cannot detect the cell nucleus in the mode for determining fluorescence signal intensity.

The term "nuclear signal intensity" refers to the signal intensity that results from the fluorescent markers that are bound to (double stranded) nucleic acids within the cell's nucleus.

The phrase "correlating the signal intensity obtained in aforementioned step b) [or step c) in the context of the method of diagnosis mentioned hereinafter] with the position and/or dimensions of the nucleus obtained in aforementioned step c) [or step d) in the context of the method of diagnosis mentioned hereinafter]" means that one superimposes the image obtained for a cell when measuring fluorescence signal strength with the phase contrast image of the same cell and then determines the signal intensity of the fluorescent marker signal being emitted from the nucleus. Superimposing the respective images and determination of nuclear signal intensity may, of course, be undertaken with well known image analysis software packages as mentioned above.

In the correlation, which may be performed using computer-based algorithms and software that is typically provided with e.g. confocal laser scanning microscopes, only those signals being emitted from the nucleus of the cells are thus taken into account. Determination of the dimensions and/or position of the nucleus using phase-contrast microscopy is necessary in order to provide the computer-based algorithm with the necessary information to disregard all signal intensities as determined in step b) which do not originate from the cell nucleus, but rather from other cellular structures such as the cytoplasm.

The reason for making this correlation is that the fluorescent markers in accordance with the invention which are capable are specifically interacting with double stranded nucleic acids will lead to a fluorescence signal not only the cell nucleus, but throughout the cell although the signal originating from the cell nucleus will be stronger given that most double stranded nucleic acids are found in the form of chromosomal DNA within the cell nucleus.

As signals arising from e.g. double stranded nucleic acid molecules in the cytoplasm of a cell will negatively impact determination of e.g. the DNA content of a cell nucleus, the methods of the present invention uses only signals which are emitted from the cell nucleus. This increases significantly the accuracy of e.g. DNA content measurement.

However, as the dimension and/or position of the cell nucleus is not determined using rather laborious staining methods as has been done in the prior art, but phase-contrast microscopy, the time needed to perform the method in accordance with the invention is significantly reduced.

Thus, the combination of using fluorescent markers which specifically can interact with double stranded nucleic acids and phase-contrast microscopy in order to determine the position and/or dimensions of a cell nucleus and the subsequent limitation of the fluorescence signal that is to be considered to such fluorescence signals that are emitted from the cell nucleus allows for a rapid and easy determination of the amount of double stranded nucleic acids within a cell nucleus and consequently detection of cancerous cells within a biological sample.

By restricting the signal intensity to be considered to the signal intensity emitted from the nucleus of a potentially cancerous cell within a biological sample using phase contrast microscopy, the method in accordance with the invention allows for a fast and accurate determination of the amount of double stranded nucleic acids within a cell nucleus as will be explained in the following.

The markers discussed herein may be exactly those markers which have been mentioned above in detail. Fluorescent marker selected from the group comprising agents binding to the major or minor DNA groove, 4',6'-diamidino-2-phenylindole (DAPI), Propidium Iodide (PI), Ethidium bromide or SYBR green may be preferred. Ethidium Bromide may be particularly preferred as it allows inter alia to detect cancerous cells that are associated with epithelial cancer in a biological brush biopsy sample.

The method of detecting at least one cancerous cell in a biological sample by using fluorescent markers which are specific for double stranded nucleic acids in combination with phase-contrast microscopy as described above allows to speed up DNA-cytometry methods as compared to e.g. the Feulgen staining method.

Through the phase contrast microscopy step it is possible to precisely locate the nucleus and to determine its dimension and to then use this information for further DNA content determination by considering only the fluorescence signal as it is emitted from the nucleus of the cells under examination. As phase-contrast microscopy is used for determining the position and/or dimensions of the nucleus it is not necessary to stain the nucleus in a second reaction which will also be time-consuming and laborious.

Given that the nucleus size and position is determined by phase-contrast microscopy, the DNA content measurement can be based on the fluorescence signal being emitted from the nucleus and thus no accuracy of DNA cytometry measurement is lost. As fluorescence staining methods are a matter of minutes and as phase-contrast measurement is a matter of seconds, DNA image cytometry measurements are performed on a significantly faster time track than the previously known DNA image cytometry approaches. In some embodiments of the present invention, the present invention thus enables measurement of DNA content of cells even in a doctor's office.

In one embodiment of the present invention, the cancerous cells may be associated with a cancer selected from the group comprising leukemia, lymphoma, brain cancer, cerebrospinal cancer, bladder cancer, prostate cancer, breast cancer, cervical cancer, uterus cancer, ovarian cancer, kidney cancer, oral and throat cancer, esophagal cancer, lung cancer, colonorectal cancer, pancreatic cancer, and melanoma.

The present invention thus provides inter alia a method for detecting at least one cancerous cell in a biological sample by using a fluorescent marker which is capable of interacting with double stranded nucleic acids within a cell. By performing phase-contrast microscopy one determines the position and/or dimensions of the nucleus. This latter information can then be correlated by e.g. using appropriate software packages with the signal intensity of the fluorescent marker as obtained for the whole cell in e.g. overlay pictures so that only the signal originating from the cell nucleus is used for the further calculations. Once one has obtained the nuclear signal intensity of the fluorescent marker of the putative at least one cancerous cell, this nuclear signal intensity is referenced to a standard nuclear signal intensity obtained by the same method for a comparable or identical cell type which is known to be non-cancerous and for which the ploidy state (2 or 4) is known in the form of a densitogram. A significant deviation from the values of the 2 or 4 or the peak areas of the reference densitogram is then considered to be indicative of cancerous development A person skilled in the art will be aware that the order of steps as discussed above may be changed. Thus, one can start by first contacting and incubating the sample with fluorescent markers, performing phase contrast microscopy and then determining the fluorescence signal intensity. In certain circumstances, it may also be possible to e.g. first perform phase contrast microscopy, then contact and incubate the sample with the fluorescent marker and finally to measure the fluorescent signal intensities.

Alternatively step c) may proceed step a) and step d) may follow step b).

Determination of Ploidy State

In the following, it will be described how the nuclear UV absorbance/nuclear signal intensities as obtained in Embodiment 1, Embodiment 2 or according to any of the other embodiments mentioned above can be used to determine the (putative) cancerogenic state of a cell.

It is common knowledge that most mammalian cells comprise a double set of each chromosome. Thus, the number of chromosomes may be calculated as 2n with n being the number of chromosomes. However, as cells replicate they double the number of chromosomes before separation of chromosomes into the daughter cells occurs.

During DNA replication and prior to cell division, mammalian cells will thus comprise a number of chromosomes that can be calculated as 4n with n being again the number of chromosomes.

If the DNA amount of a mammalian cell is referenced to the number of chromosome, the DNA content of a non-cancerous cell which may also be designated as "healthy" or "normal" cell may thus assigned the values 2 or 4 depending on the replication state of the cell.

The term "ploidy state" in the context of the present invention refers to the DNA content of a normal, non-cancerous cell and may have the values of 2 and 4 as explained above.

It is also common knowledge in the art how to determine the ploidy state of a non-cancerous cell by e.g. using the aforementioned Feulgen staining method. In this context, the publication of Hardie et al. (The Journal of Histochemistry & Cytochemistry (2002), 50(6), 735-749) is incorporated by reference as far as it describes the determination of DNA content of a cell using DNA staining methods.

In the section "Image Analysis Densitometry" on page 738 of the Hardie et al. reference it is explained how the signal intensities obtained by e.g. the Feulgen staining method or fluorescent markers or UV absorption signals can be converted into densitometric values. As explained above a healthy, non-cancerous cell will comprise 2n or 4n chromosomes with n being the number of chromosomes. Thus, densitometric analysis of signal intensities as obtained from the nuclear UV absorption signals as used in the present invention will lead to a densitometric profile with two peaks areas.

These two peak areas will be assigned the values of 2 or 4, respectively (if the cell is proliferating). An example of such a densitometric profile is provided in FIG. 1. In the specific case, a non-proliferating cell population was analysed which explains why there is no peak corresponding to 4. If for a cell population of the same tissue which typically is also known to be non-proliferative, a value of 4 would be observed, this would be indicative of proliferation and in this situation cancerous state.

Briefly, for image analysis densitometry, the microscope field which one uses for viewing the cells and measuring the nuclear UV signal is captured by a microscope-mounted CCD (charge coupled device) detection device or a digital camera that are connected to a computer. The pictures being digitalized images are recorded as a series of pixels, each pixel being assigned a characteristic colour and intensity. The intensities are then typically converted by computer-based algorithms into absorbance values, which in turn are displayed by an image analysis software as the aforementioned densitograms.

The person skilled in the art is, of course aware, that a meaningful and reliable densitogram of normal, non-cancerous cells should be preferably calculated from a population of numerous cells with a number of preferably 25-100 cells typically being sufficient. In a preferred embodiment of the invention, the amount of nuclear DNA will thus be determined by measuring the nuclear UV absorbance as described above for approximately at least 30, 40, 50 or 60 cells.

In a further embodiment of the present invention, the nuclear UV absorption may be used to detect cancerous cells in at least one biological sample. The nuclear signal intensity of the fluorescent marker being bound to nuclear double stranded nucleic acids as obtained according to the aforementioned Embodiment 2 may, of course, also be used to detect at least one cancerous cell in at least one biological sample.

This is achieved by determining the nuclear DNA content or ploidy state of the putative cancerous cells using the above-described methods in accordance with the invention. The determined ploidy state is then compared with the ploidy state of non-cancerous cells for which ploidy state has been determined from nuclear signal intensities obtained by the identical method.

For determining of whether a putative cancerous cell is indeed a cancer-prone cell one will thus determine a densitogram as described above. The densitogram observed for non-cancerous cells will be designated as the "standard" or "reference" densitogram.

Preferably, such reference densitograms will be measured using the same method as for detecting the cancerous cells, but one will ensure that only non-cancerous cells are used. This may be achieved by using cells of the same individual but from other tissue sites than those that are suspected to be cancerous. Alternatively or additionally one may use identical or comparable cell types, but from a different individual which is known to be not afflicted by cancer. If cells of the same individual are used, one should preferably use comparable cell types as long as it is ensured that these cells are non-cancerous. The number and type of cells to be studied in order to obtain a standard densitogram (i.e. histogram) are well within the knowledge of the person skilled in the art and will vary between 25 and 100 cells and preferably around 30, 40 50 or 60 cells.

For the purposes of the present invention, the term "comparable cell Type" thus relates to a cell type that is of comparable origin and has comparable cellular characteristics as the suspected cancerous cell. If for example a mucosal cell will be tested for cancer development, the standard reference cell should also be of mucosal origin. If on the other side lymphoid cells are tested for cancer developments, the standard reference cell should be also of lymphoid origin in order to be a comparable cell type Typical standard or comparable cell types may thus be lymphocytes, granulocytes, normal epithelial cells or stromal cells.

The nuclear UV absorbance/nuclear intensity of the comparable cell type which is known to be non-cancerous and which is used as a standard reference for the nuclear signal intensity obtained for the putative cancerous cell should be measured under highly similar if not identical conditions, if possible.

Thus, the comparable cell type, which may also be designated as standard or reference cell should be prepared and isolated from a comparable biological probe and fixed and permeabilized (if necessary) substantially identical as cells under analysis. Furthermore, reference cells should be analyzed during the same run as the actual cancerous cells using the same microscope conditions.

If for a certain cell, a ploidy state is determined which deviates from the aforementioned values of 2 or 4, this is indicative of either substantial duplications, insertions, deletions or chromosomal rearrangements and thus of cancerous cells. As in this case, the ploidy state of such a cell deviates from the values of 2 and 4; one also speaks of the aneuploidy state. This, of course, assumes that one consider a cell type which is typically proliferative even in its normal state.

Thus, a ploidy value of 4 may be indicative of cancer development if one examines cells that are usually known to be non-proliferative.

If one examines cells which are known to be proliferative in their normal state a value of 4 will not considered to be indicative for cancer-development. In this case only deviations from the values of 2 and 4 will be indicative of cancer development.

The term "aneuploidy state" in the context of the present invention thus relates to an abnormal amount of nuclear DNA within a cell.

To obtain reliable, the amount of nuclear DNA and thus the densitogram (histogram) of putatively cancerous cells will preferably be calculated from a population of cells and one preferably will measure approximately 100 to 700 and preferably around 100 to 300 cells.

Figure 2:
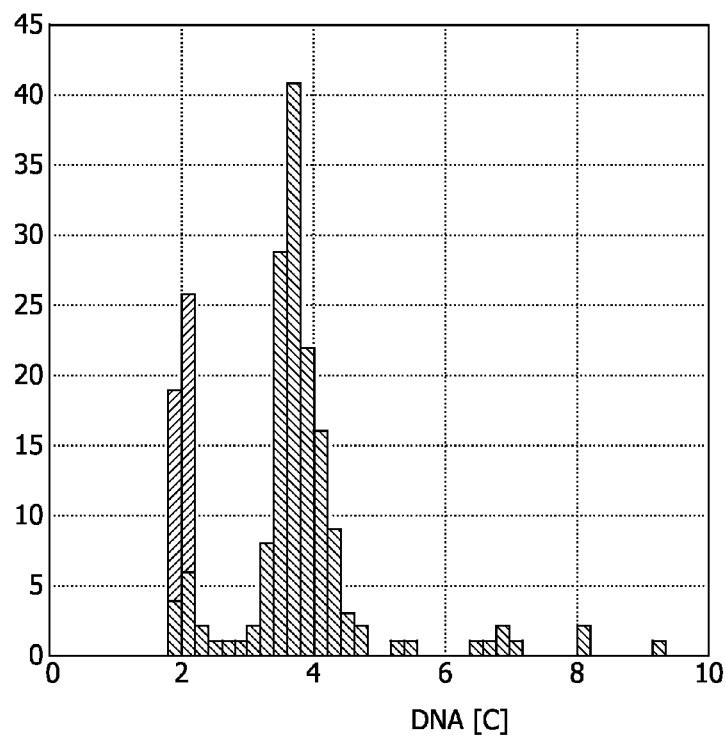
FIG. 2 shows a histogram profile, i.e. a densitometric profile as typically obtained if nuclear DNA content of a population of cancerous cells is determined. The peak corresponding to the value of 4 is indicative of ongoing cancer development as a cell type is examined which in its normal state is non-proliferative.

If one examines e.g. cancerous cells from liver tissue, one will e.g. obtain a densitogram with two main peaks, which are assigned the values of 2 and 4. However, other than in the case of non-cancerous cells the two main peaks densitogram will not be as sharp and narrow but rather broad. Additionally one will observe peaks and signals in the densitogram that are below 2, above 2, below 4 and above 4. An example is provided in FIG. 2.

Since the majority of cells in any sample will have a DNA content of 2, deviation from the majority could also be considered as abnormal or suspicious. In the event of a cancerous sample, where normal cells are in the minority, there will still be a large variance in the DNA content that can be used to label the sample as suspicious.

A cell will therefore be rated as cancerous if the densitogram that is calculated on the basis of the nuclear UV absorption which are obtained in accordance with the invention as described above, shows peak signals outside the peaks corresponding to the values 2 (and 4, depending on the proliferative state of the cell in its normal state).

However, the peaks corresponding to the values of 2 (and 4) may themselves be indicative for cancerous potential of a cell, if they show a rather broad curvature. In order to decide whether a densitogram is indeed indicative for cancer development or not in view of the peak form corresponding to values 2 (and 4), one will superimpose the densitogram of a putative cancerous cell sample with a standard or reference densitogram as described above.

The areas under the curve (AUC) of the peaks of the densitograms being indicative of the values 2 and 4 of the standard densitogram are taken as being indicative of a non-cancerous cell and any deviations the AUCs of the corresponding peaks of the densitogram of the putative cancerous cell by at least 10% will be considered to be indicative of a cancerous cell or state. In a preferred embodiment the deviation will be at least 15%, at least 20%, at least 25%, at least 30%, at least 40% or at least 50%.

One may also apply the standards set forth in the publication of Haroske et. al. "1997 *ESACP consensus report on diagnostic DNA image cytometry*", Analytical Cellular Pathology 17 (1998) 189-200 where it is explained in detail when a cell will be considered to be normal or cancerous.

Thus, a significant deviation of the nuclear UV absorption/nuclear signal intensity of a suspected cancerous cell (population) in comparison to the nuclear UV absorption obtained for a comparable non-cancerous cell type is indicative of either ongoing or likely future cancer development.

For the purposes of the present invention, a significant aberration in DNA content will be considered to be indicative of cancer development if the ploidy state of the suspected cancerous cells deviates from the ploidy values of 2 (and 4, if the cell in its healthy state is proliferating) by at least 10%. In a preferred embodiment the deviation will be at least 15%, at least 20%, at least 25%, at least 30%, at least 40% or at least 50%. A peak in a densitogram will have assigned a value of 2 or 4 for this part of the peak that is identical with the corresponding peaks in a reference densitogram.

In accordance with established practice, one may designate the DNA content of a cell as peridiploid if the peak corresponding to peak value 2 of the reference densitogram ranges from 1.8 to 2.2.

The DNA content of a cell will be considered to be peritetraploid if the peak corresponding to peak value 4 of the reference densitogram ranges from 3.6 to 4.4.

Any values outside these ranges will be considered as X-ploid.

Cells and tissues with peripdiploid, peritetraploid and x-ploid values will considered as cancerous cells for the purposes of the present invention.

Thus, the above-described method can be used to calculate the ploidy (aneuploidy) state of a putative cancerous cell in a biological sample by referencing the nuclear UV absorption as obtained in accordance with the method of the invention for the putative cancerous cell with a nuclear UV absorption using the same approach for a comparable cell type which is known to be non-cancerous.

For the purposes of the present invention, the term "non-cancerous" refers to a cell, which is known to show no indications of cancer development.

In one embodiment of the present invention, the cancerous cells may be associated with a cancer selected from the group comprising leukaemia, lymphoma, brain cancer, cerebrospinal cancer, bladder cancer, prostate cancer, breast cancer, cervical cancer, uterus cancer, ovarian cancer, kidney cancer, oral and throat cancer, oesophageal cancer, lung cancer, colon rectal cancer, pancreatic cancer, and melanoma.

Methods of Diagnosis

As mentioned above, the present invention also relates to an in vitro method of diagnosing and/or predicting cancer in a human or animal subject is provided which comprises steps of:
- a) providing a biological sample from a human or animal subject;
- b) determining the position and/or dimensions of the nucleus within at least one cell of said sample in vitro,
- c) measuring in vitro the UV absorbance within the nucleus' boundaries as determined in a),
- d) calculating from the nuclear signal intensity obtained in step d) the ploidy state of said at least one cell,
- e) deciding on the presence aand/or likely future occurrence of a cancer depending the ploidy state.

The methods of diagnosis in accordance with the present invention also comprises various embodiments which realize the basic concept of determining the position and/or dimensions of the nucleus within a cell and determining the UV absorbance within the nucleus' boundaries. For determining the nucleus position and/or dimensions which is equivalent to determining the nucleus' boundaries one can again use phase contrast microscopy with visible light as well as detection approaches with UV light. For determining the UV absorbance of the nucleus one may rely solely on UV measurements without adding fluorescent markers that are capable of interacting with double stranded nucleic acids or one may use such markers.

In the following, general aspects of these methods of diagnosis will be discussed. Further issues will be discussed with respect to two specific embodiments. The skilled person understands that certain aspects of these two embodiments which will be discussed in closer detail can nevertheless similarly applied to other of the embodiments envisaged above.

As regards step a), a biological sample may be obtained from a human or animal subject using conventional methods such as for example brush biopsies, aspirates, fine needle aspirate biopsies, endoscopic biopsies etc.

Steps b), c) and d) may then be performed as steps a) and b) of the above-described method of determining in vitro the amount of nuclear double stranded nucleic acids within a cell which can preferably be applied to detect at least one cancerous cell within a biological sample.

In a last step which has been designated above as step e), one decides on the presence or likely future occurrence of cancer depending on the nuclear DNA content or ploidy state of the cells under examination. This last step will be discussed in closer detail after the two embodiments have been presented.

Of course, the explanations given above as to the determination of densitograms for the putative cancerous cell and reference or standard densitograms, the meaning of terms such as "in vitro", "approximately", "ploidy", "aneuploidy", "peridiploid", "peritetraploid", "X-ploid", "AUC" etc. equally apply in the context of the method of diagnosis and/or prevention of cancer in accordance with the invention.

The term "in vitro" means that all steps of the above method of diagnosis are done without direct contact to the human or animal body.

Embodiment 1—Method of Diagnosis

In one exemplary embodiment the present invention relates to an in vitro method of diagnosing and/or predicting cancer in a human or animal subject which comprises the steps of:
- a) obtaining a biological sample comprising at least one cell from the subject;
- b) determining in vitro the position and/or dimensions of the nucleus within said cell;
- c) determining in vitro the UV absorption within the nucleus boundaries as determined in b) using UV light;
- d) calculating from the nuclear UV absorption obtained in step c) the nuclear DNA content or ploidy state of said at least one cell and
- e) deciding on the presence or likely future occurrence of a cancer depending on the nuclear DNA content or the ploidy state.

Steps b) and c) may be performed as steps a) and b) of the above-described Embodiment 1 of determining in vitro the amount of nuclear double stranded nucleic acids within a cell which can preferably be applied to detect at least one cancerous cell within a biological sample.

In a preferred embodiment of these aspects of the invention, one uses UV light of a wavelength between approximately 240 nm and approximately 280 nm for measuring UV absorbance in steps a) and/or b). Particularly preferred are wavelengths such as approximately 250 nm, 255 nm or 260 nm.

Step d) may also be performed as described above.

In a last step which has been designated above as step e), one decides on the presence or likely future occurrence of cancer depending on the nuclear DNA content or ploidy state of the cells under examination.

In performing this method of diagnosis and/or predicting cancer, the same procedures for isolating the biological sample, for preparing the cellular samples, for contacting the cells in question possibly with a fluorescent marker, for determining the signal intensities may be used.

Thus, in a preferred embodiment one will use confocal laser scanning microscopy for identifying the nucleus boundaries and measuring nuclear UV absorbance. To this end, one may use e.g. the instruments described above.

Embodiment 2—Method of Diagnosis

In another exemplary embodiment the present invention relates to an in vitro method of diagnosing and/or predicting cancer in a human or animal subject which the steps of:
- a) obtaining a biological sample from the subject;
- b) contacting said at least one cell with at least one fluorescent marker which is capable of interacting with double stranded nucleic acids within said at least one cell outside the body of the subject;
- c) determining the signal intensity of said at least one fluorescent marker being bound to double stranded nucleic acids with the signal being obtained by excitation with a suitable light source;
- d) determining the position and/or dimensions of the nucleus within said at least one cell by phase-contrast microscopy;
- e) determining the nuclear signal intensity of fluorescent marker being bound to nuclear double stranded nucleic acids by correlating the signal intensity obtained in c) with the position and/or dimensions of the nucleus obtained in d).
- f) calculating from the nuclear signal intensity obtained in step e) the nuclear DNA content or ploidy state of said at least one cell
- g) deciding on the presence or likely future occurrence of a cancer depending on the nuclear DNA content or the ploidy state.

Steps b) to e) may be performed as steps a) to d) of the above-described Embodiment 2 of determining the amount of nuclear double stranded nucleic acids within a cell which can preferably be applied to detect at least one cancerous cell within a biological sample.

Step f) may also be performed as described above.

In a last step which has been designated above as step g), one decides on the presence or likely future occurrence of cancer depending on the nuclear DNA content or ploidy state of the cells under examination.

In performing this method of diagnosis and/or predicting cancer, the same procedures for isolating the biological sample, for preparing the cellular samples, for contacting the cells in question with the fluorescent marker, for determining the signal intensities, for performing phase-contrast microscopy as outlined above for the method of determining the amount of double stranded nucleic acids within a cell nucleus may be used.

Thus, the fluorescent marker may be any molecule which is capable of specifically interacting with double stranded nucleic acids and which provides a fluorescent signal upon excitation with a suitable light source.

Such fluorescent markers may bind e.g. to the major or minor DNA grooves. They may be nucleic acid base-intercalating agents and can be be selected from the group comprising 4',6'-diamidino-2-phenylindole (DAPI), Propidium Iodide (PI) and Ethidium bromide (EtBr). Fluorescent markers also include SYBR green.

A person skilled in the art will be aware that the order of steps as discussed above may be changed. Thus, one can start by first contacting and incubating the sample with fluorescent markers, performing phase contrast microscopy and then determining the fluorescence signal intensity. In certain circumstances, it may also be possible to e.g. first perform phase contrast microscopy, then contact and incubate the sample with the fluorescent marker and finally to measure the fluorescent signal intensities.

In one embodiment of the invention, the method of diagnosing and/or predicting cancer in a human or animal subject relies in essence of the afore-mentioned steps with step d) preceding steps b) to c) and step c) being followed by steps e), f) and g).

Method of Diagnosis—Evaluation

In the above mentioned methods, in the last step e) (or g) in case of Embodiment 2) a decision is made on the presence of likely future occurrence of cancer.

A cancer diagnosis may be considered as positive if the nuclear DNA content or ploidy values as determined for the cells of the biological sample obtained from the subject deviates by at least 10% from the nuclear DNA content or ploidy values of 2 (and 4, if the cell in its normal state is proliferating) of a comparable cell type for which the nuclear signal intensity has been measured under highly comparable or an identical condition and which is known to be non-cancerous. In a preferred embodiment the deviation will be at least 15%, at least 20%, at least 25%, at least 30%, at least 40% or at least 50%.

The areas under the curve (AUC) of the peaks being indicative of the values 2 and 4 of a standard densitogram are taken as being indicative of a non-cancerous cell and any deviations the AUCs of the corresponding peaks of the densitogram of the putative cancerous cell by at least 10% will be considered to indicative of a cancerous cell and thus will lead to a positive diagnosis. In a preferred embodiment the deviation will be at least 15%, at least 20%, at least 25%, at least 30%, at least 40% or at least 50%.

In accordance with established practice, one will designate the DNA content of a cell as peridiploid if the peak corresponding to peak value 2 of the reference densitogram ranges from 1.8 to 2.2.

The DNA content of a cell will be considered to be peritetraploid if the peak corresponding to peak value 4 of the reference densitogram ranges from 3.6 to 4.4.

Any values outside these ranges will be considered as X-ploid.

Cells with peridiploid, peritetraploid and x-ploid values will considered as cancerous cells for the purposes of the present invention and accordingly a positive cancer diagnosis will be made if the DNA content is considered to be peridiploid, peritetradiploid or X-ploid.

The in vitro method of diagnosing and/or predicting cancer may be used to diagnose and/or predict a cancer selected from the group comprising leukaemia, lymphoma, brain cancer, cerebrospinal cancer, bladder cancer, prostate cancer, breast cancer, cervical cancer, uterus cancer, ovarian cancer, kidney cancer, oral and throat cancer, oesophageal cancer, lung cancer, colon rectal cancer, pancreatic cancer, and melanoma.

The method of diagnosis and/or predicting cancer may be used to analyse samples selected from the group comprising bone marrow cells, lymph node cells, lymphocytes, erythrocytes, neural cells, muscle cells, fibroblasts, keratinocytes, mucosal samples, peripheral blood samples, cerebrospinal fluid samples, urine samples, effusion samples, fine needle aspirates, fine needle aspiration biopsies, peripheral blood scrapings, skin scrapings, smears from exfoliated cells, cytocentrifuged preparations from body fluids, cell separation specimen (after mechanic and/or enzymatic dispersions), paraffin embedded tissues and frozen sections.

In the following certain aspects of the invention relating to the above described embodiments 1 and 2 are put forth specifically:

Embodiment 1—Certain Aspects

1. Method of determining in vitro the amount of nuclear nucleic acids in at least one cell being present in at least one biological sample comprising the steps of:
    a) determining the position and/or dimensions of the nucleus within said cell in vitro,
    b) measuring in vitro the UV absorbance within the nucleus' boundaries as determined in a) using UV.
2. Method according to 1.,
    wherein the position and/or dimensions of the nucleus within said at least one cell is determined by using UV light and/or phase-contrast microscopy.
3. Method according to 1. or 2.,
    wherein UV light of a wavelength between approximately 240 nm and approximately 280 nm is used in step a) and/or b).
4. Method according to 3.,
    wherein UV light of a wavelength of approximately 250 nm, 255 nm or 260 nm is used in step a) and/or b).
5. Method according to any of numbers 1. to 4. wherein the nuclear nucleic acids are not visualized with an immunohistochemical stain, a chemical reaction or a fluorescent marker.
6. Method according to any of numbers 1. to 5.,
    wherein the method is used to detect at least one putative cancerous cell in said at least one biological sample.
7. Method according to any of numbers 1. to 6.,
    wherein the at least one cancerous cell is associated with a cancer selected from the group comprising leukemia, lymphoma, brain cancer, cerebrospinal cancer, bladder cancer, prostate cancer, breast cancer, cervical cancer, uterus cancer, ovarian cancer, kidney cancer, oral and throat cancer, esophageal cancer, lung cancer, colon rectal cancer, pancreatic cancer, and melanoma.
8. Method according to 6.,
    wherein the nuclear UV absorbance in step b) is used to calculate the nuclear DNA content or ploidy state of the putative cancerous cell by comparing the nuclear UV absorbance obtained in step b) with the nuclear UV absorbance of at least one non-cancerous cell which has been analysed also using steps a) and b) of claim 1.

9. Method according to 8.,
wherein a deviation in ploidy state or nuclear DNA content by at least 10% from the values of 2 is indicative of a cancerous cell.

10. Method according 8.,
wherein a ploidy state or nuclear DNA content of 1.8 to 2.2 is indicative of a peridiploid state, a ploidy state or nuclear DNA content of 3.6 to 4.4 is indicative of a peritetraploid state and a ploidy state or nuclear DNA content outside these ranges is indicative of an X-ploid state.

Embodiment 2—Certain Aspects

1. Method of determining the amount of nuclear double stranded nucleic acids in at least one cell being present in at least one biological sample comprising the steps of:
   a) contacting said at least one cell with at least one fluorescent marker which is capable of interacting with double stranded nucleic acids within said at least one cell;
   b) determining the signal intensity of said at least one fluorescent marker being bound to double stranded nucleic acids with the signal being obtained by excitation with a suitable light source;
   c) determining the position and/or dimensions of the nucleus within said at least one cell by phase-contrast microscopy;
   d) determining the nuclear signal intensity of fluorescent marker being bound to nuclear double stranded nucleic acids by correlating the signal intensity obtained in b) with the position and/or dimensions of the nucleus obtained in c).

2. Method according to 1.,
wherein the method is used to detect at least one putative cancerous cell in said at least one biological sample.

3. Method according to 2.,
wherein the nuclear signal intensity obtained in step d) is used to calculate the nuclear DNA content or ploidy state of the cell by comparing the signal intensity obtained in step d) with the nuclear signal intensity of a non-cancerous cell which has been obtained also using steps a) to d) of claim 1.

4. Method according to 1.,
wherein a deviation in ploidy state or nuclear DNA content by at least 10% from the values of 2 or 4 is indicative of a cancerous cell.

5. Method according 4.,
wherein a ploidy state or nuclear DNA content of 1.8 to 2.2 is indicative of a peridiploid state, a ploidy state or nuclear DNA content of 3.6 to 4.4 is indicative of a tetradiploid state and a ploidy state or nuclear DNA content outside these ranges is indicative of an X-ploid state.

6. Method according to 2.,
wherein the at least one cancerous cell is associated with a cancer selected from the group comprising leukemia, lymphoma, brain cancer, cerebrospinal cancer, bladder cancer, prostate cancer, breast cancer, cervical cancer, uterus cancer, ovarian cancer, kidney cancer, oral and throat cancer, esophagal cancer, lung cancer, colonorectal cancer, pancreatic cancer, and melanoma.

7. Method according to 1.,
wherein the biological sample is selected from the group comprising bone marrow cells, lymph nodes cells, mucosal samples, peripheral blood, cerebrospinal fluid, urine, effusions, fine needle aspirates, peripheral blood scrapings, skin scrapings, paraffin embedded tissues, and frozen sections.

8. Method according to 1.,
wherein the fluorescent marker is selected from the group comprising against agents binding to the major or minor DNA groove, 4',6'-diamidino-2-phenylindole (DAPI), Propidium Iodide (PI), Ethidium bromide, SYBR green, SYTOX Blue, SYTOX Green, SYTOX Orange, POP-1, BOBO-1, YOYO-1, TOTO-1, JOJO-1, POPO-2, LOLO-1, BOBO-1, YOYO-3, TOTO-3, PO-PRO-1, BO-PRO-1, TO-PRO-1, JO-PRO-1, PO-PRO-3, LO-PRO-1, BO-PRO-3, YO-PRO-3, TO-PRO-3, TO-PRO-5, SYTO 40 blue-fluorescent nucleic acid stain, SYTO 41 blue-fluorescent nucleic acid stain, SYTO 42 blue-fluorescent nucleic acid stain, SYTO 43 blue-fluorescent nucleic acid stain, SYTO 44 blue-fluorescent nucleic acid stain, SYTO 45 blue-fluorescent nucleic acid stain, SYTO 9 green-fluorescent nucleic acid stain, SYTO 10 green-fluorescent nucleic acid stain, SYTO 11 green-fluorescent nucleic acid stain, SYTO 12 green-fluorescent nucleic acid stain, SYTO 13 green-fluorescent nucleic acid stain, SYTO 14 green-fluorescent nucleic acid stain, SYTO 15 green-fluorescent nucleic acid stain, SYTO 16 green-fluorescent nucleic acid stain, SYTO 20 green-fluorescent nucleic acid stain, SYTO 21 green-fluorescent nucleic acid stain, SYTO 22 green-fluorescent nucleic acid stain, SYTO 23 green-fluorescent nucleic acid stain, SYTO 24 green-fluorescent nucleic acid stain, SYTO 25 green-fluorescent nucleic acid stain, SYTO 26 green-fluorescent nucleic acid stain, SYTO 27 green-fluorescent nucleic acid stain, SYTO BC green-fluorescent nucleic acid stain, SYTO 80 orange-fluorescent nucleic acid stain, SYTO 81 orange-fluorescent nucleic acid stain, SYTO 82 orange-fluorescent nucleic acid stain, SYTO 83 orange-fluorescent nucleic acid stain, SYTO 84 orange-fluorescent nucleic acid stain, SYTO 85 orange-fluorescent nucleic acid stain, SYTO 86 orange-fluorescent nucleic acid stain, SYTO 17 red-fluorescent nucleic acid stain, SYTO 59 red-fluorescent nucleic acid stain, SYTO 61 red-fluorescent nucleic acid stain, SYTO 17 red-fluorescent nucleic acid stain, SYTO 62 red-fluorescent nucleic acid stain, SYTO 63 red-fluorescent nucleic acid stain, SYTO 64 red-fluorescent nucleic acid stain, Acridine homodimer, Acridine orange, 7-AAD (7-amino-actinomycin D), Actinomycin D, ACMA, DAPI, Dihydroethidium, Ethidium Bromide, Ethidium homodimer-1 (EthD-1), Ethidium homodimer-2 (EthD-2), Ethidium monoazide, Hexidium iodide, Hoechst 33258 (bis-benzimide), Hoechst 33342, Hoechst 34580, Hydroxystibamidine, LDS 751 and Nuclear yellow.

9. Method according to 1.,
wherein the fluorescent marker Ethidium Bromide is used to detect a cancerous cell that is associated with oral epithelial cancer in a biological brush biopsy sample.

10. A method of diagnosing and/or predicting cancer in a human or animal subject comprising the steps of:
   a) obtaining a biological sample from the subject;
   b) contacting said at least one cell with at least one fluorescent marker which is capable of interacting with double stranded nucleic acids within said at least one cell outside the body of the subject;
   c) determining the signal intensity of said at least one fluorescent marker being bound to double stranded nucleic acids with the signal being obtained by excitation with a suitable light source;

d) determining the position and/or dimensions of the nucleus within said at least one cell by phase-contrast microscopy;

e) determining the nuclear signal intensity of fluorescent marker being bound to nuclear double stranded nucleic acids by correlating the signal intensity obtained in c) with the position and/or dimensions of the nucleus obtained in d).

f) calculating from the nuclear signal intensity obtained in step e) the ploidy state of said at least one cell deciding on the presence or likely future occurrence of a cancer depending the ploidy state.

In the following, the invention is illustrated in view of certain experimental examples. These examples are however in no way meant to limit the invention as to its scope, but rather serve to illustrate the invention by way of some of its exemplary embodiments.

EXPERIMENTS

Experiment 1

DNA Image Cytometry Measurement on Semi-Fixed Cells

Figure 3:
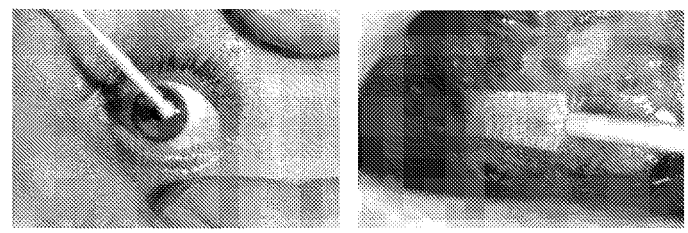
FIG. 3 shows examples of brush biopsies in the eye (left picture) and the mouth (right picture).

In a first step, a sample can be taken for instance via a brush biopsy (see FIG. 3).

In a second step, the cells are then eluted from the brush by rinsing the sample taken unit with e.g. a physiological buffer such as PBS pH 7.4.

In a third step, the cells may be made permeable for staining by addition of a mild detergent like Triton X-100. For this purpose, one may for example use a buffer comprising PBS pH 7.4, 0.05% (w/v) Triton X-100. In case of a (semi)-fixed cell approach, the cell suspension can be applied to a microscopy slide and be allowed to dry for immobilisation.

In the next step, one then can perform e.g. a fluorescence measurement by illuminating the microscopic slides with a LEICA EL6000 light source-emitting wavelength from 300 to 600 nm. One can for example use a 450 nm source.

By scanning through the cell one can determine the position of the nucleus.

The nuclear UV absorption may then be recorded using Qimaging Retiga 2000R FASTCooled Mono 12-bit camera unit (www.qimaging.com).

If this nuclear UV absorption is compared with the DNA content as obtained under identical conditions for a cell which is known to be non-cancerous, one can calculate the ploidy state of the cells under examination and decide whether the cells are likely to develop cancer or not.

Experiment 2

DNA Image Cytometry Measurement on Semi-Fixed Cells

In a first step, a sample can be taken for instance via a brush biopsy (see FIG. 3).

In a second step, the cells are then eluted from the brush by rinsing the sample taken unit with e.g. a physiological buffer such as PBS pH 7.4.

In a third step, the cells may be made permeable for staining by addition of a mild detergent like Triton X-100. For this purpose, one may for example use a buffer comprising PBS pH 7.4, 0.05% (w/v) Triton X-100. In case of a (semi)-fixed cell approach, the cell suspension can be applied to a microscopy slide and be allowed to dry for immobilisation.

The cellular DNA can then be stained by addition of a fluorescence intercalator dye such as Ethidium bromide. As this and many other fluorescent dyes have a much stronger fluorescence when bound to DNA, it may be not necessary to wash the free dye away. However, washing may be performed if it allows to improve the signal to background ratio.

Figure 6:
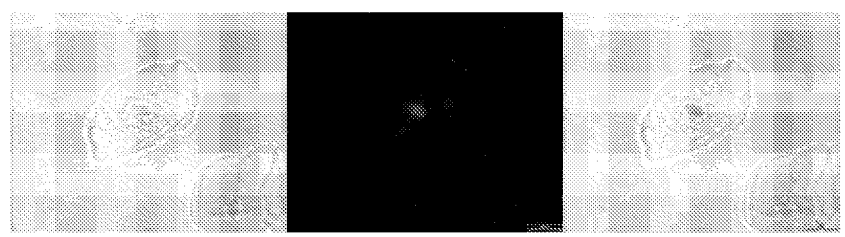
FIG. 6 shows measurement of the fluorescence for mucosal cells which have been stained with EtBr. The cell nucleus is clearly visible, however, also the other parts of the cell show some fluorescence.

In the next step, one then can perform e.g. a fluorescence measurement by illuminating the microscopic slides with a LEICA EL6000 light source emitting wavelength from 300 to 600 nm. One can for example use a 488 nm source. (see FIG. 6) The fluorescence signal emitted may then be recorded using Qimaging Retiga 2000R FASTCooled Mono 12-bit camera unit (www.qimaging.com).

Figure 7:
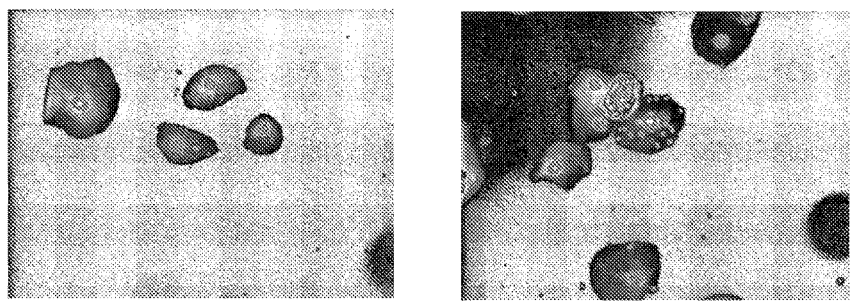
FIG. 7 shows a phase-contrast image (left picture), fluorescence image (middle picture) and the combined image (right picture) of a mucosal cell which has been stained with EtBr. Merging and correlating the phase-contrast microscopy image with a fluorescence image allows to precisely determine the nucleus position and its dimensions.

In another step, the same samples are then recorded under phase-contrast microscopy in order to identify the position and/or dimensions of the nucleus (see FIG. 7).

In a further step, the images obtained by the fluorescence and phase-contrast microscopy are merged so that only the fluorescent signal originating from the nucleus is recorded (see FIG. 7).

If this signal is compared with the DNA content as obtained under identical conditions for a cell which is known to be non-cancerous, one can calculate the ploidy state of the cells under examination and decide whether the cells are likely to develop cancer or not.

The invention claimed is:

1. A method for detecting a ploidy state of a cell of interest in a biological tissue sample without fluorescent markers that interact with double stranded nucleic acids, the method comprising:
   scanning through a single plane of the biological tissue sample, wherein the first scan traverses the cell of interest, and wherein the first scan traverses the cell's nucleus and non-nuclear portions of the cell of interest;
   measuring an ultraviolet (UV) light absorbance within the nuclear and non-nuclear portions of the cell of interest during the first scan;
   scanning through at least a second plane of the biological tissue sample, wherein the second scan traverses the cell of interest, and wherein the second scan traverses nuclear and non-nuclear portions of the cell of interest;
   measuring the UV light absorbance within the nuclear and non-nuclear portions of the cell of interest during the second scan;
   reconstructing a three-dimensional (3D) volume of the nucleus of the cell of interest from the combined scans, wherein a ratio between the measurement for the UV nuclear absorption versus the UV non-nuclear absorption from each plane is taken as a calibrated measurement for the UV absorption of the cell nucleus; and
   determining the ploidy state of the cell of interest from the UV absorbance of the whole nucleus and the reconstructed 3D volume, wherein a measure for UV absorption of the whole nucleus is obtained by summing up the calibrated measurements of the scans.

2. The method according to claim 1, wherein UV light of a wavelength of from 240 nm to 280 nm.

3. The method according to claim 1, wherein UV light of a wavelength of approximately 250 nm, 255 nm or 260 nm.

4. The method according to claim 1 wherein the biological sample is prepared without any of an immunohistochemical stain or a chemical reaction.

5. The method according to claim 1, wherein the ploidy state is averaged over 25 to 100 cells of interest in the biological sample.

6. The method according to claim 1, wherein the cells of interest are cancer cells selected from the group consisting of leukemia, lymphoma, brain cancer, cerebrospinal cancer, bladder cancer, prostate cancer, breast cancer, cervical cancer, uterus cancer, ovarian cancer, kidney cancer, oral and throat cancer, esophageal cancer, lung cancer, colon rectal cancer, pancreatic cancer and melanoma.

* * * * *